United States Patent
Yeon et al.

(10) Patent No.: US 8,855,259 B2
(45) Date of Patent: Oct. 7, 2014

(54) SYSTEM AND METHOD FOR DETECTING LEAKAGE OF NUCLEAR REACTOR COOLANT USING LASER INDUCED EMISSION SPECTRUM

(75) Inventors: Jei-Won Yeon, Daejeon (KR); Kyuseok Song, Daejeon (KR); Euo-Chang Jung, Daejeon (KR)

(73) Assignee: Korea Atomic Energy Research Institute (KR)

( * ) Notice: Subject to any disclaimer, the term of this patent is extended or adjusted under 35 U.S.C. 154(b) by 1026 days.

(21) Appl. No.: 12/963,343

(22) Filed: Dec. 8, 2010

(65) Prior Publication Data

US 2011/0164715 A1  Jul. 7, 2011

(30) Foreign Application Priority Data

Dec. 9, 2009 (KR) .................. 10-2009-0121829

(51) Int. Cl.
| G21C 17/00 | (2006.01) |
| G01J 3/443 | (2006.01) |
| G01N 21/71 | (2006.01) |
| G21C 17/02 | (2006.01) |

(52) U.S. Cl.
CPC .............. *G21C 17/002* (2013.01); *G21C 17/02* (2013.01); *G01J 3/443* (2013.01); *G01N 21/718* (2013.01)
USPC ........................................................ 376/250

(58) Field of Classification Search
CPC .............................. G21C 17/002; G21C 17/02
USPC ........................................................ 376/250
See application file for complete search history.

(56) References Cited

U.S. PATENT DOCUMENTS

| 4,135,972 | A | | 1/1979 | Anthony et al. |
| 4,925,307 | A | * | 5/1990 | Cremers et al. ............... 356/318 |
| 4,933,138 | A | | 6/1990 | Mouesca et al. |
| 5,345,479 | A | | 9/1994 | Graham |
| 5,608,520 | A | * | 3/1997 | Fleming ........................ 356/318 |
| 5,751,416 | A | * | 5/1998 | Singh et al. ................... 356/311 |
| 2002/0149768 | A1 | * | 10/2002 | Sabsabi et al. ............... 356/318 |
| 2003/0174325 | A1 | * | 9/2003 | Zhang et al. ................. 356/318 |

(Continued)

FOREIGN PATENT DOCUMENTS

| EP | 0808681 | * 11/1997 |
| JP | 2002341081 A1 | 11/2002 |
| JP | 2008096345 A | 4/2008 |
| KR | 100356153 B1 | 9/2002 |

OTHER PUBLICATIONS

Web page "Who Laser Analysis Works?", version dated Dec. 3, 2008, science.howstuffworks.com/laser-analysis.htm.*

(Continued)

*Primary Examiner* — Frank J McGue
(74) *Attorney, Agent, or Firm* — Fredrikson & Byron, P.A.

(57) ABSTRACT

System and method for detecting and/or predicting in a field the leakage of nuclear reactor coolant that may occur at the pressure boundary of the primary system of a nuclear reactor. The system and method for detecting the leakage of nuclear reactor coolant uses a laser induced emission spectrum. The leakage of coolant is detected by detecting boron (B), a main component of the coolant, in corrosive products generated at the nuclear reactor pressure boundary on the basis of laser spectroscopy. An embodiment of the system for detecting leakage of nuclear reactor coolant may include a laser generator, a laser focusing lens, an emission collector, and emission spectrum analyzer.

17 Claims, 4 Drawing Sheets

(56) References Cited

U.S. PATENT DOCUMENTS

2003/0223529 A1 12/2003 de la Penna et al.
2009/0014635 A1* 1/2009 Neitsch .................. 250/252.1
2012/0099103 A1* 4/2012 Hahn ..................... 356/316

OTHER PUBLICATIONS

Web page "What is Laser Induced Breakdown Spectroscopy?", version dated Jun. 22, 2007, www.art.army.mil/www/default.cfm?Action247&Page=247.*
Whitehouse et al., "Extreme LIBS", @2002 OSA/LIBS 2002.*
Aoki, K., "Reactor coolant pressure boundary leak detection systems in JapanesePWR plants," Nuclear Engineering and Design 128 (1991), pp. 35-42.
Kupperman, D.S. et al., "Evaluation of methods for leak detection in reactor primary systems," Nuclear Engineering and Design 89 (1985), pp. 371-378.
Kupperman, D.S. et al., "Acoustic leak detection for reactor coolant systems," Nuclear Engineering and Design 86 (1985) pp. 13-20.
Aoki, K., "Reactor coolant pressure boundary leak detection systems in Japanese PWR plants," Nucl. Eng. and Design 128 (1991) pp. 35-42.
Kupperman, D.S., et al., "Evaluation of methods for leak detection in reactor primary systems," Nucl. Eng. and Design 89 (1985), pp. 371-378.
Kupperman, D.S., et al., "Acoustic leak detection for reactor coolant systems," Nucl. Eng. and Design 86 (1985) pp. 13-20).

* cited by examiner

SYSTEM AND METHOD FOR DETECTING LEAKAGE OF NUCLEAR REACTOR COOLANT USING LASER INDUCED EMISSION SPECTRUM

RELATED APPLICATIONS

This application claims priority to Korean Application No. KR 10-2009-0121829 filed Dec. 9, 2009, the teachings of which are incorporated herein by reference.

BACKGROUND OF THE INVENTION

1. Field of the Invention

The present invention relates, in general, to a measurement system and method for analyzing the components of impurities generated at the pressure boundary of the primary system of a nuclear reactor.

2. Description of the Related Art

Current methods of detecting the leakage of nuclear reactor coolant in a nuclear power plant include methods which are disclosed in Korean Pat. No. 10-0356153 (Sep. 27, 2002) and reported in Nuclear Engineering and Design, (1), (1985) by Kupperman, D. S. and which use sound waves or ultrasonic waves. Other nuclear coolant reactor coolant detection methods have been reported, and include one detection method that uses the detection of a sump level and that is reported in Nuclear Engineering and Design, (1), (1991) by Aoki, K., another leakage detection system that uses a difference between the flow rates of ultrasonic flow meters and that is disclosed in Japanese Pat. Laid-Open Publication No. 2002-341081A (Nov. 27, 2002), and the other coolant leakage detection method and apparatus that is disclosed in U.S. Pat. No. 5,345,479 (Sep. 6, 1994.) and Japanese Pat. Laid-Open Publication No. 2008-96345A (Apr. 24, 2008) and that detects radioactive substances generated when coolant leaks.

In spite of these conventional leakage detection methods, it is currently very difficult to detect the leakage of a coolant either in advance or when the amount of coolant leaked is small. Therefore, to date, in order to accurately determine whether leakage has occurred, a condition allowing an operator to access a relevant leakage location is made by disassembling surrounding parts of the nuclear reactor, removing the materials and units surrounding the pressure boundary of the nuclear reactor when the nuclear reactor is overhauled, and thereafter the operator inspects a predicted coolant leakage location with the naked eye.

Meanwhile, commercialized methods capable of analyzing the components of metal compounds in the field may include mobile X-ray fluorescence analysis. However, this method makes it difficult to analyze elements having a small atomic weight, such as boron. There is a disadvantage in that in order to analyze elements having a small atomic weight, the atmosphere between the sample and the detector must be controlled. Further, there is a limitation in that it is difficult to apply such methods to highly radioactive environments such as the surroundings of a nuclear reactor, or to samples having high radiation levels.

SUMMARY OF THE INVENTION

Accordingly, the present invention has been made in consideration of the fact that the main component of nuclear reactor coolant is boron and that when the coolant leaks, the coolant evaporates, but boron remains at the leakage location in the form of deposits, together with radioactive corrosion products, and an object of the present invention is to provide an apparatus and method that promptly detects boron atoms contained in the radioactive corrosion products and impurities generated at the pressure boundary of the nuclear reactor which is inaccessible due to the high radiation level thereof, thus promptly detecting the leakage of the coolant and predicting possible leakage locations in advance.

In accordance with an aspect of the present invention to accomplish the above object, there is provided an apparatus for detecting leakage of nuclear reactor coolant, comprising a laser generator for generating laser beam; a laser focusing lens for focusing the laser beam generated by the laser generator; an emission collector for inducing a plasma emission on a target material when the laser beam focused by the laser focusing lens is concentrated, and collecting light from the induced plasma emission; and an emission spectrum analyzer for analyzing the light of the plasma emission collected by the emitted light collector.

Preferably, the laser generator comprises a laser generation unit, an attenuator for adjusting intensity of the laser beam generated by the laser generation unit, an energy meter for measuring energy intensity of the laser beam adjusted by the attenuator, and a refraction unit for changing a path of the generated laser beam.

Preferably, the laser beam generated by the laser generator has a form of pulses.

Preferably, the laser generation unit is a laser having a power of 0.5 mJ or more.

Preferably, the laser beam focused by the laser focusing lens has a diameter that is greater than 0 and is equal to or less than 5 mm.

Preferably, the laser beam focused by the laser focusing lens has a diameter that is greater than 0 and is equal to or less than 3 mm.

Preferably, the emitted light collector is a lens or an optical fiber for collecting light.

Preferably, the emitted light collector is located within a range from 0.5 to 100 cm around the plasma emission induced on the target material.

Preferably, the emitted light collector is located within a range from 1 to 20 cm around the plasma emission induced on the target material.

Preferably, an analysis wavelength used to analyze boron in the emission spectrum analyzer ranges from 200 to 600 nm.

Preferably, an analysis wavelength used to analyze boron in the emission spectrum analyzer ranges from 200 to 350 nm.

In accordance with another aspect of the present invention, there is provided an apparatus for detecting leakage of nuclear reactor coolant, comprising a laser generator for generating laser beam; a laser focusing lens for focusing the laser beam generated by the laser generator; an emission collector for inducing a plasma emission on a target material when the laser beam focused by the laser focusing lens is concentrated, and collecting light from the induced plasma emission; an emission spectrum analyzer for analyzing the light of the plasma emission collected by the emitted light collector; and an ultrasonic generation laser or a compressed air jetting device for temporarily eliminating water from surroundings of the target material.

Preferably, the apparatus further comprises a suction filter for eliminating impurities from surroundings of the emitted light collector.

Preferably, the impurities are volatile materials or separated fine particles generated during induction of the plasma emission.

In accordance with a further aspect of the present invention, there is provided a method of detecting leakage of nuclear reactor coolant, the method being performed using an apparatus for detecting leakage of nuclear reactor coolant, which includes a laser generator for generating laser beam; a laser focusing lens for focusing the laser beam generated by the laser generator; an emission collector for inducing a plasma emission on a target material when the laser beam focused by the laser focusing lens is concentrated, and collecting light from the induced plasma emission; and an emission spectrum analyzer for analyzing the light collected by the emitted light collector, comprising a) causing at least the laser focusing lens and the emitted light collector of the apparatus to approach the target material; b) controlling a focal distance of the laser beam with respect to the target material after a); c) after the focal distance has been controlled, radiating the laser beam onto the target material; d) collecting light of a plasma emission induced on the target material at c) by using the emitted light collector; and e) analyzing the collected light.

Preferably, e) is performed using a relative ratio of intensity of an emission line of only iron (Fe) in the emission spectrum to intensity of an overlapping emission line of boron (B) and iron.

Preferably, e) is performed using an emission line of 249.773 nm.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, embodiments of the present invention will be described in detail with reference to the attached drawings. Reference now should be made to the drawings, in which the same reference numerals are used throughout the different drawings to designate the same or similar components. When the present invention is described, detailed descriptions of the related well-known functions or constructions will be omitted to prevent the gist of the present invention from being unclear.

The present invention, in its various embodiments, provides systems and methods for detection and analysis of impurities generated at the pressure boundary of the primary system of nuclear reactor. According to some embodiments, the system and method of the invention detect the leakage of nuclear reactor coolant that may occur in nuclear power plants and predicted early. In some embodiments, the system and method for detecting and predicting the leakage of nuclear reactor coolant using a laser induced emission spectrum, which is implemented as an apparatus including a laser generator, a laser focusing lens, an emission collector, and an emission spectrum analyzer. The system can have the function of improving the current inconvenience of disassembling the surrounding parts of a nuclear reactor and inspecting them with the naked eye.

Figure 1:
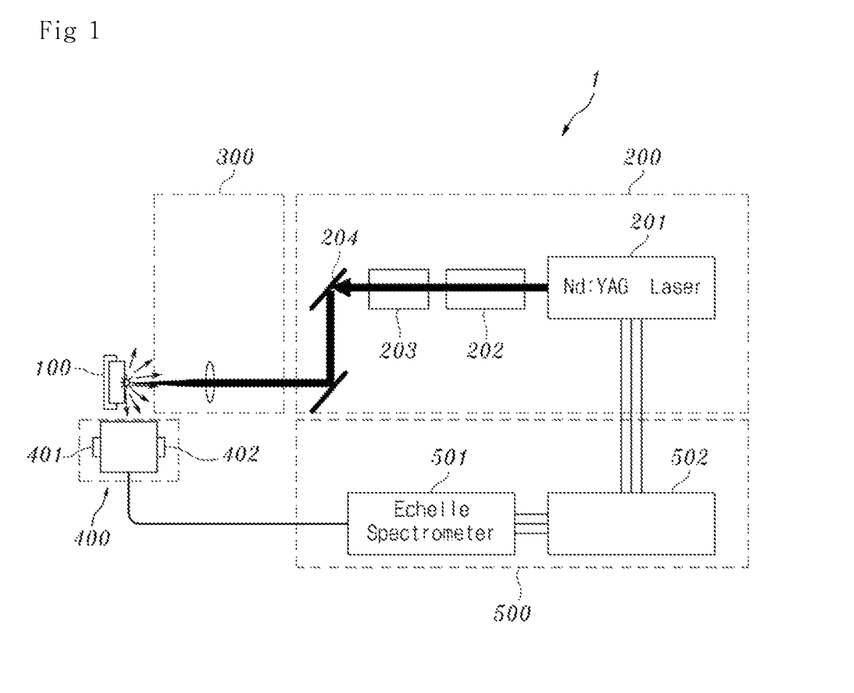
FIG. 1 is a diagram showing an apparatus for detecting the leakage of nuclear reactor coolant using a laser induced emission spectrum according to the present invention.

FIG. 1 is a diagram showing the construction of an apparatus for detecting the leakage of nuclear reactor coolant.

As shown in FIG. 1, an apparatus 1 for detecting the leakage of nuclear reactor coolant (hereinafter shortly referred to as a "leakage detection apparatus") according to an embodiment of the present invention includes a laser generator 200, a laser focusing lens 300, an emission collector (an emitted light collector) 400, and an emission spectrum analyzer 500. The leakage detection apparatus 1 can be used for the purpose of checking components of various types of impurities generated by a nuclear reactor coolant system while having the characteristics of promptly detecting/predicting the leakage of nuclear reactor coolant by detecting boron elements, which are main chemical components of the coolant, in radioactive deposits generated at the pressure boundary.

The present invention is a system for condensing laser beam having high energy, emitted from the laser generator 200, onto deposits and impurities, that is, a target material 100, generated at the pressure boundary of the nuclear reactor which is structurally inaccessible to an operator, inducing plasma on the surface of the target material 100, and analyzing the emission spectrum of the plasma, thus analyzing the components of the deposits and impurities. In this case, to facilitate the induction of plasma on the target material 100 by using the laser beam emitted from the laser generator 100, it is profitable to generate the laser beam in the form of pulses rather than continuous waves. The generated laser beam is condensed onto the target material 100 using the laser focusing lens 300, and light produced by the induced plasma is analyzed by the emission spectrum analyzer 500 via the emitted light collector 400 in the form of a spectrum indicating intensities at respective wavelengths. In particular, the presence of the boron elements, which are main components of the coolant, in corrosion products and impurities is determined, and thus the leakage of the coolant is promptly detected and predicted.

When laser beam collides with the target material 100, a shock wave is generated while part of the target material 100 is ablated, and, simultaneously, plasma may be generated. The present invention analyzes the presence of the components of the target material 100, in particular, boron elements, using a plasma emission generated from among various types of phenomena induced by laser beam, and then detects the leakage of the coolant.

As an embodiment of the present invention, the laser generator includes a laser generation unit 201 for generating laser beam, an attenuator 202 for attenuating the intensity of the generated laser beam to a level suitable for the radiation onto the target material 100 by adjusting the intensity of the generated laser beam, an energy meter 203 for measuring the intensity of the laser beam attenuated by the attenuator 202 in relation to whether the attenuated intensity is suitable for radiating the laser beam onto the target material 100 and generating a plasma emission, and a refraction unit 204 for guiding the path of the laser beam generated by the laser generation unit 201 to the laser focusing lens 300.

The refraction unit 204 may be implemented using a plurality of lenses or reflectors.

The function of the laser focusing lens 300 of the leakage detection apparatus 1 according to the present invention facilitates the generation of plasma on the surface of the target material 100 by focusing the laser beam emitted from the laser generator 200. As the diameter of the laser beam focused on the surface of the target material 100 becomes smaller, the energy concentration of the laser beam becomes higher. It can be seen from the results of experiments that when the laser generation unit 201 is implemented as a 266 nm Nd:YAG laser at 10 mJ, the generation of plasma is facilitated and it is not difficult to maintain the precision of analysis in the case where the diameter of the focused laser beam is equal to or less than 1 mm.

When the power of the high-power laser that is typically handled is taken into consideration, the case where the diameter of the focused laser beam is equal to or less than 3 mm is effective in generating plasma and maintaining the precision of analysis.

In the present invention, the emitted light collector 400 is a device for collecting light generated from plasma (or emission light) so as to obtain an emission spectrum, and has the form of a lens or an optical fiber because it collects light. Generally, as a sensor is located far away from a signal generation source, sensitivity is in inverse proportion to the cube of the distance. Therefore, in order to maintain analyzable sensitivity, the emitted light collector 400 must be located as close to the location at which the plasma is generated as is possible, which should be within a range from 0.5 to 100 cm. As the emitted light collector 400 is located closer to the target material 100, the higher sensitivity of analysis is obtained. However, when volatile materials are generated or when separated fine particles are sprayed into the surroundings during the generation of the plasma, these may damage the optical parts of the emitted light collector 400, thus shortening its lifespan. Accordingly, the emitted light collector 400 must be preferably present within a range from 1 to 20 cm around the plasma generation location.

Since secondary pollution is possible during an analysis procedure, the leakage detection apparatus 1 may further include a suction filter 401 for eliminating volatile materials or fine particles from the surroundings of the emitted light collector 400.

Further, the present invention can analyze the target material 100 even when the target material 100 is present in water as long as an ultrasonic generation laser or a compressed air jetting device 402 capable of temporarily eliminating water from the surroundings of the target material 100 is also provided.

When plasma is generated by laser beam radiated onto the corrosion products generated at the pressure boundary, that is, the target material 100, and light of plasma of various wavelengths is input to the emission spectrum analyzer 500 via the emitted light collector 400, the intensity of emission is analyzed by various optical devices depending on the wavelengths of light.

The emission spectrum analyzer 500 includes an Echelle spectrometer 501 and a data processing unit 502 for analyzing the relative emission intensity of boron so as to determine whether the target material 100 contains boron (B), using data about the emission spectrum measured by the spectrometer 501. The data processing unit 502 may be implemented using a typical Personal Computer (PC).

Figure 2:
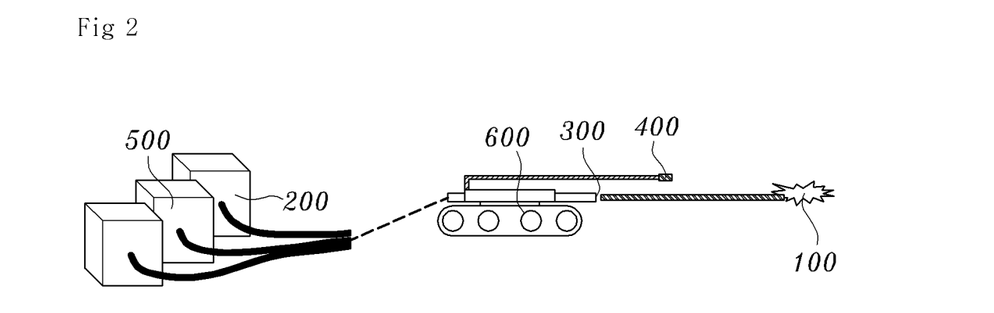
FIG. 2 is a conceptual diagram showing the application of an apparatus for detecting the leakage of nuclear reactor coolant according to the present invention.

FIG. 2 is a conceptual diagram showing the application of the nuclear leakage detection apparatus according to the present invention.

As shown in FIG. 2, the leakage detection apparatus 1 of FIG. 1 according to an embodiment of the present invention causes both the laser focusing lens 200 and the emitted light collector 300 to move close to the deposit of the pressure boundary of the nuclear reactor, which is the target material 100, by using a transfer device 600.

The transfer device 600 may be an integrated device including both the laser focusing lens 200 and the emitted light collector 300 or may adopt the form of the laser focusing lens 200 and the emitted light collector 300 being detachably mounted.

The laser generation unit 200, located outside the pressure boundary and spaced apart from the target material 100, generates laser beam. The generated laser beam is radiated onto the target material 100 through the laser focusing lens 200 which is moved close to the target material 100 by the transfer device 600.

Further, plasma is generated on the target material 100 by the radiated laser beam, and the light of the generated plasma is collected by the emitted light collector 300 installed near the target material 100.

The emission spectrum of the light collected by the emitted light collector 300 is analyzed by the emission spectrum analyzer 500 which is located outside the pressure boundary and spaced apart from the target material 100, and thus whether or not boron is contained in the target material 100 is analyzed.

As described above, the present invention relates to an apparatus for determining using laser beam whether boron elements which are the main components of the nuclear reactor coolant are present in deposits generated at the nuclear reactor pressure boundary at the time of detecting the leakage of the nuclear reactor coolant, thus promptly detecting the leakage of the coolant.

Hereinafter, the present invention will be described in detail using preferred embodiments of the present invention. It is apparent that the accompanying embodiments are merely intended to help the understanding of the present invention and the present invention is not limited to the embodiments.

Figure 3:
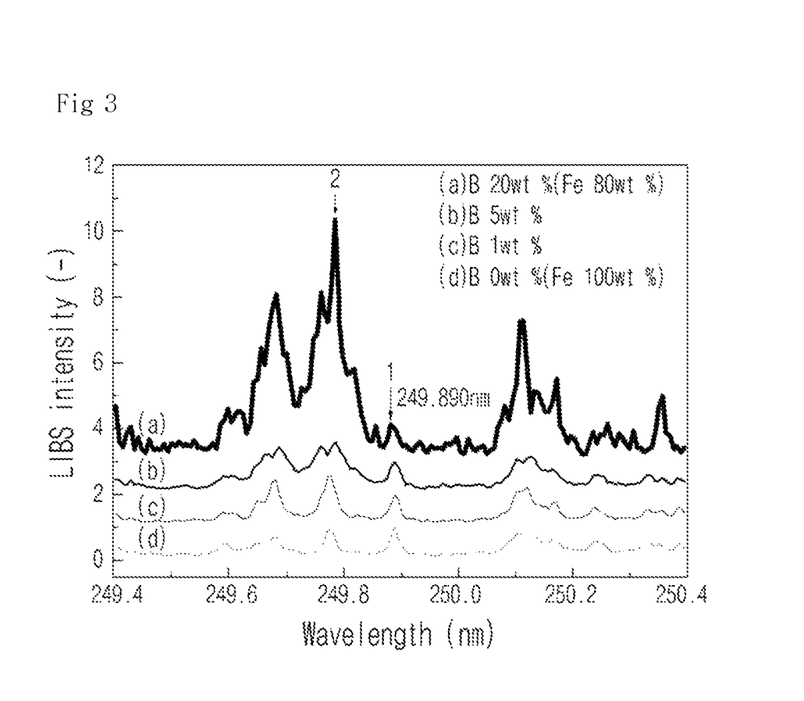
FIG. 3 is a graph showing the laser induced emission (plasma) spectrum of an iron oxide containing boron of various concentrations according to the present invention.

FIG. 3 is a graph showing the laser induced emission (plasma) spectrum of an iron (Fe) oxide containing boron at various concentrations according to the present invention.

After an iron oxide target material 100 containing boron at various concentrations has been prepared for, content of boron (B) in the iron oxide is checked via chemical analysis (Inductively Coupled Plasma Atomic Emission Spectroscopy: ICP-AES) at the same time that the components of boron (B) in the iron oxide are being measured using a laser induced emission spectrum.

Among four sequential curves shown in the graph of FIG. 3, a higher curve indicates a sample containing a higher concentration of boron (B) in the target material 100.

The ablation spectrum by laser pulse do not have uniform intensity of light emission, since the degree of laser ablation varies depending on conditions of measurement such as laser incident angle, ingredient of sample, or the like. Also, it is uneasy to conduct boron analysis only with the intensity of emission lines of boron on the spectrum, since most main emission lines of boron (B) in the emission spectrum overlap the emission lines of iron (Fe).

Therefore, according to one embodiment, only one emission line of iron (Fe) is set as the internal reference, and characteristic emission lines of boron (B) at 249.773 nm are selected respectively, so that presence or absence of boron (B) is determined by determining a relative ratio of the peak intensity of boron (B) with respect to peak intensity of iron (F).

Referring to FIG. 3, in order to analyze boron (B) in the emission spectrum, the intensity of one specific characteristic wave at 249.890 nm (i.e., a spot indicated by arrow No. 1) of iron (F) is set as the internal reference, and the relative ratio of the intensity of emission line of boron (B) at 249.773 nm (a spot indicated by arrow No. 2) with respect to the internal reference (i.e., ratio between boron peak intensity and iron peak intensity) is obtained. If the obtained relative ratio is greater than a value computed from the iron oxide, it is possibly determined that the target material 100 contains boron (B).

Figure 4:
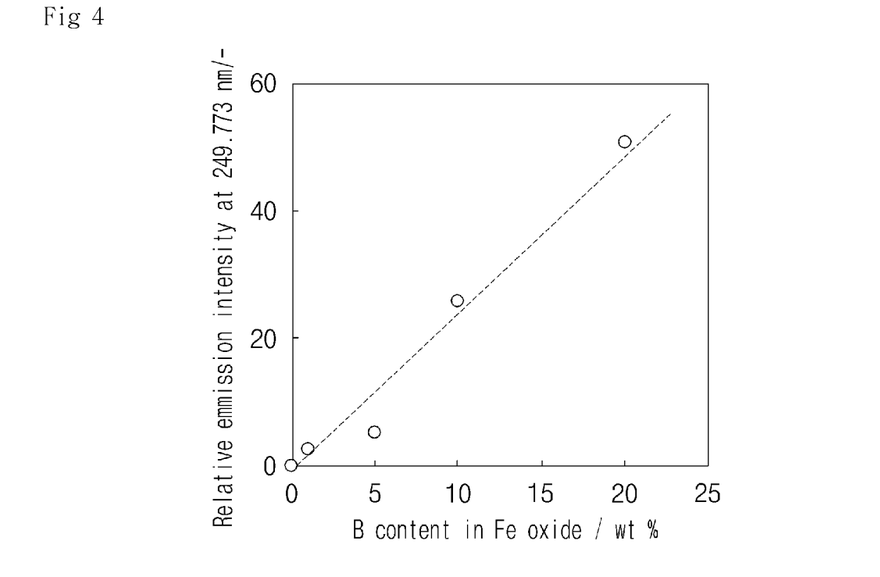
FIG. 4 is a graphical representation of the correlation between boron content in iron oxide and a ratio of boron characteristic peak intensity versus iron characteristic peak intensity in ablation spectrum (i.e., ratio between peak intensity at 249.773 nm and peak intensity at 249.890 nm)

FIG. 4 is a graphical representation of the correlation between boron content in iron oxide and a ratio of boron characteristic peak intensity versus iron characteristic peak intensity in ablation spectrum (i.e., ratio between peak intensity at 249.773 nm and peak intensity at 249.890 nm), which shows the boron (B) content in iron oxide obtained using the relative ratio of the emission peak of only iron (Fe) to the overlapping emission peak of boron and iron at 249.773 nm, which has been analyzed in FIG. 3.

Figure 5:
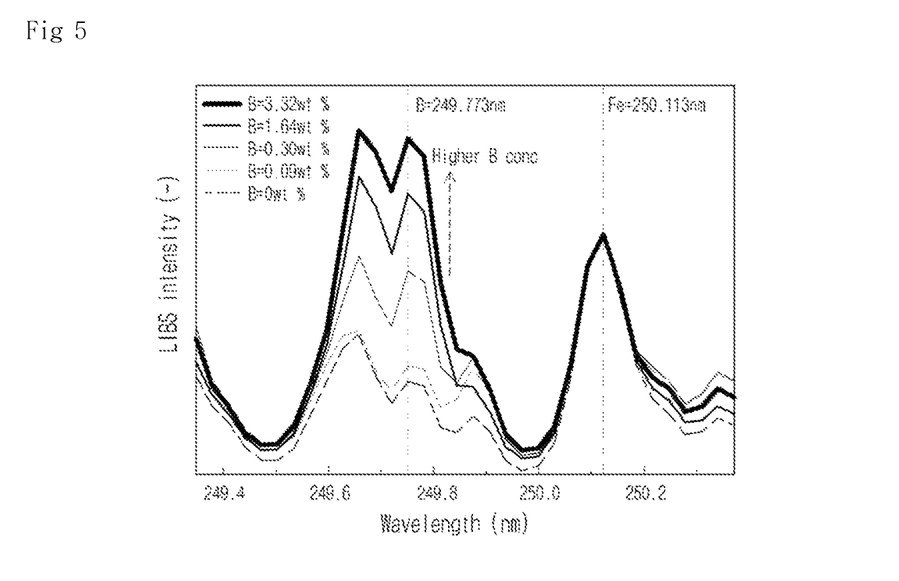
FIG. 5 is a graphical representation of a laser induced plasma spectrum of iron oxide containing boron at various concentration (below 4 wt. %) according to the present invention.

FIG. 5 provides a laser ablation spectrum of iron oxide with low boron content (<4 wt. %). For the analysis of iron oxide with low boron content, again, the emission line of boron at 249.773 m is selected. However, as for the internal reference, the emission line of iron at 250.113 nm provides more optimum result than at 249.890 nm in this analysis.

Figure 6:
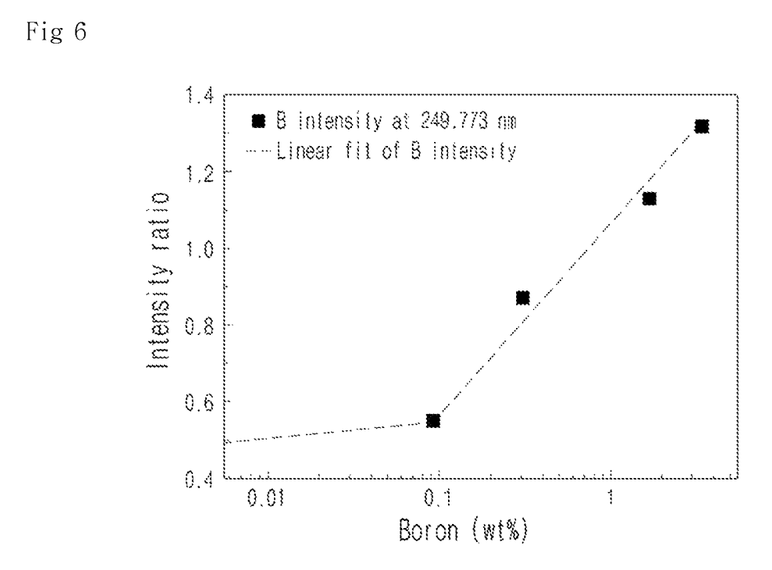
FIG. 6 is a graphical representation of a correlation between boron content in iron oxide and a ratio of boron characteristic peak intensity versus iron characteristic peak intensity (i.e., peak intensity at 249.773 nm/peak intensity at 250.113 nm) in ablation spectrum.
Figure 7:
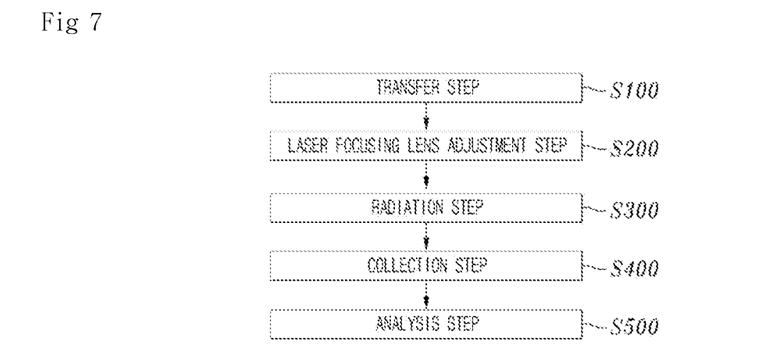
FIG. 7 is a flowchart illustrating a method of detecting the leakage of nuclear reactor coolant according to the present invention.

FIG. 6 is a graphical representation of a correlation between boron content in iron oxide and a ratio of boron characteristic peak intensity versus iron characteristic peak intensity (i.e., peak intensity at 249.773 nm/peak intensity at 250.113 nm) in ablation spectrum, according to which it is possible to detect the minimum detection limit of boron and the boron content.

As explained above, it was confirmed that boron content in iron oxide can be measured using laser induced emission spectrum based on a relationship between relative emission intensities using internal reference The wavelength of 249.773 nm is a representative emission wavelength of boron (B), and is also called an emission line. There are a few other emission lines of boron (B), and moreover, they overlap iron lines that have high emission intensity over a wide wavelength range. Accordingly, it can be proven via experiments that the boron emission line of 249.773 nm is the most suitable one to use for the analysis of boron. Additionally, depending on the boron content, the iron emission line may se 249.890 nm or 250.113 nm for use as the internal reference.

If even a slight defect occurs at the pressure boundary of the nuclear reactor, high-temperature high-pressure coolant flows out through the defect, and is then leaked in the form of vapor. Since the nuclear reactor coolant contains a large amount of boron, boron remains in the form of deposits around the location of leakage when the boron leaks in the form of vapor. In contrast, boron is not detected in corrosion products generated at places where leakage does not occur. Therefore, if there is even a small amount of boron that can be detected by the nuclear reactor coolant leakage detection apparatus and method according to the present invention, it will be able to reason that coolant leakage has occurred.

Whether coolant has leaked can be sufficiently determined as long as only the presence of boron is determined. However, the graphs in FIGS. 3 and 4 can also be used to predict the velocity or amount of coolant that has leaked, on the basis of the intensity of the boron wavelength of the analyzed sample, that is, the target material 100.

FIG. 5 is a flowchart showing a method of detecting the leakage of nuclear reactor coolant according to the present invention.

The nuclear reactor coolant leakage detection method according to an embodiment of the present invention includes steps S100 to S500. At step S100 which is the transfer step, in the nuclear reactor coolant leakage detection apparatus 1 of FIG. 1 according to the present invention including the laser generator 200 for generating laser beam; the laser focusing lens 300 for focusing the laser beam generated by the laser generator 200; the emitted light collector 400 for inducing a plasma emission on a target material 100 when the laser beam focused by the laser focusing lens 300 is condensed, and collecting light from the induced plasma emission; and the emission spectrum analyzer 500 for analyzing the light collected by the emitted light collector 400, at least the laser focusing lens 300 and the emitted light collector 400 are caused to approach the location near the target material 100. At step S200 which is the laser focusing lens adjustment step, the focal distance of laser beam is controlled with respect to the target material 100 after the transfer step S100. After the laser focusing lens adjustment step S200, at step S300 which is the radiation step, laser beam is radiated onto the target material 100. At step S400 which is the analysis step, light of plasma emission induced on the target material 100 at radiation step S300 is collected by the emitted light collector 400. At step S500 which is the analysis step, the collected light is analyzed.

At transfer step S100, locating at least the laser focusing leans 300 and the emitted light collector 400 near the target material 100 creates favorable conditions to focus laser beam and collect light from the induced plasma emission. For this, a small-sized transfer device 600 that employs a wheel, a caterpillar, a rail, etc. and that is operable in a wired or wireless manner can be used. The laser focusing lens 300, the emitted light collector 400, etc. can be attached to the transfer device 600.

The attachment of the laser focusing lens 300 and the emitted light collector 400 to the transfer device 600 may be implemented either detachably or an integration manner.

It is also possible to allow the laser generator 200 or the emission spectrum analyzer 500 to be spaced apart from the target material 100 and to be located outside the pressure boundary.

Analysis step S500 is performed using the relative ratio of the emission intensity of an iron oxide to the emission intensity of an iron oxide containing boron (B), and it can be reasoned that when the relative ratio has a positive value, the target material 100 contains boron (B). Since the emission line of boron is most suitable at a wavelength of 249.773 nm, the 249.773 nm emission line is preferably used at analysis step S500.

As described above, a large amount of boron ($H_3BO_3$) is contained in nuclear reactor coolant. The present invention analyzes in a field the presence of boron (B) elements in corrosion products that are generated outside the pipes of the pressure boundary of the primary system of a nuclear reactor, thus promptly detecting and predicting the leakage of the nuclear reactor coolant. Further, the present invention can promptly identify the components of various types of impurities generated in a nuclear reactor coolant system.

The present invention is advantageous in that the leakage of a coolant can be determined by detecting deposits of boron, the main component of the coolant, and that laser technology enabling remote control is used for such detection. Therefore, there is no need to disassemble the nuclear reactor and the surrounding parts of pipes so as to inspect the leakage of the coolant, and in that the present invention has functions of analyzing deposits in a field via remote control and determining whether the coolant has leaked by radiating laser beam onto the location of the generation of the deposits, without undergoing difficulties in collecting and handling a radioactive samples.

Although the preferred embodiments of an apparatus and method for detecting the leakage of nuclear reactor coolant according to the present invention have been described with reference to illustrated drawings, those skilled in the art will appreciate that various modifications, additions and substitutions are possible, without departing from the scope and spirit of the invention as disclosed in the accompanying claims.

What is claimed is:

1. A method of detecting leakage of nuclear reactor coolant, the method being performed using an apparatus for detecting leakage of nuclear reactor coolant, which includes a laser generator for generating laser beam; a laser focusing lens for focusing the laser beam generated by the laser generator; an emission collector for collecting light from plasma emission which is induced on a target material when the laser beam focused by the laser focusing lens is concentrated on the target material; an emission spectrum analyzer for analyzing the light collected by the emission collector, and a transfer device to which the laser focusing lens and the emission collector are attached, wherein the target material consists of depositions and impurities generated at the pressure boundary of the nuclear reactor, comprising:
   a) using the transfer device to move at least the laser focusing lens and the emission collector of the apparatus close to the target material;
   b) controlling a focal distance of the laser beam with respect to the target material after a);
   c) after the focal distance has been controlled, radiating the laser beam onto the target material;
   d) collecting light of a plasma emission induced on the target material at c) by using the emission collector; and
   e) analyzing the collected light using a relative ratio of intensity of an emission line of only iron (Fe) in the emission spectrum to intensity of an overlapping emission line of boron (B) and iron.

2. The method according to claim 1, wherein e) is performed using a ratio of intensity at 249.773 nm of the emission line of boron with respect to intensity of the emission line of iron.

3. The method according to claim 2, wherein the emission line of iron uses wavelength range from about 249.0 to about 250.5 nm.

4. The method according to claim 1, wherein the laser generator comprises:
   a laser generation unit:
   an attenuator for adjusting intensity of the laser beam generated by the laser generation unit;
   an energy meter for measuring energy intensity of the laser beam adjusted by the attenuator; and
   a refraction unit for changing a path of the generated laser beam.

5. The method according to claim 4, wherein the laser generation unit is a laser having a power of 0.5 mJ or more.

6. The method according to claim 1, wherein the laser beam generated by the laser generator has a form of pulses.

7. The method according to claim 1, wherein the laser beam focused by the laser focusing lens has a diameter that is greater than 0 and is equal to or less than 5 mm.

8. The method according to claim 1, wherein the laser beam focused by the laser focusing lens has a diameter that is greater than 0 and is equal to or less than 3 mm.

9. The method according to claim 1, wherein the emission collector is a lens or an optical fiber for collecting light.

10. The method according to claim 1, wherein the emission collector is located within a range from 0.5 to 100 cm around the plasma emission induced on the target material.

11. The method according to claim 1, wherein the emission collector is located within a range from 1 to 20 cm around the plasma emission induced on the target material.

12. The method according to claim 1, wherein an analysis wavelength used to analyze boron in the emission spectrum analyzer ranges from 200 to 300 nm.

13. The method according to claim 1, wherein an analysis wavelength used to analyze boron in the emission spectrum analyzer ranges from 249.0 to 251.0 nm.

14. The method according to claim 1, wherein the apparatus for detecting leakage of nuclear reactor coolant further comprises ultrasonic generation laser or a compressed air jetting device for temporarily eliminating water from surroundings of the target material.

15. The method according to claim 14, wherein the apparatus further comprises a suction filter for eliminating impurities from surroundings of the emission collector.

16. The method according to claim 15, wherein the impurities are volatile materials or separated fine particles generated during induction of the plasma emission.

17. A method of detecting leakage of nuclear reactor coolant, the method being performed using an apparatus for detecting leakage of nuclear reactor coolant, which includes a laser generator for generating laser beam; a laser focusing lens for focusing the laser beam generated by the laser generator; an emission collector for collecting light from plasma emission which is induced on a target material when the laser beam focused by the laser focusing lens is concentrated on the target material; an emission spectrum analyzer for analyzing the light collected by the emitted light emission collector, and a transfer device to which the laser focusing lens and the emission collector are attached, wherein the target material consists of depositions and impurities generated at the pressure boundary of the nuclear reactor, comprising:
   a) using the transfer device to move at least the laser focusing lens and the emitted light emission collector of the apparatus close to the target material;
   b) controlling a focal distance of the laser beam with respect to the target material after a);
   c) after the focal distance has been controlled, radiating the laser beam onto the target material;
   d) collecting light of a plasma emission induced on the target material at c) by using the emitted light emission collector;
   e) analyzing the collected light using a relative ratio of intensity of an emission line of only iron (Fe) in the emission spectrum in the wavelength range from about 249.0 nm to about 250.5 nm, to intensity of an emission line of boron (B) and iron at 249.773 nm; and
   f) determining leakage of nuclear reactor coolant from the result of analyzing the collected light of e).

* * * * *